United States Patent
Tsao et al.

(10) Patent No.: US 8,377,503 B2
(45) Date of Patent: Feb. 19, 2013

(54) METHOD FOR REAL-TIME MONITORING THICKNESS CHANCE OF COATING FILM

(75) Inventors: Yu-Chia Tsao, Taipei (TW); Chung-Pei Lee, Taipei (TW); Ko-Shao Chen, Taipei (TW); Jia-Huey Tsao, Yingge Township, Taipei County (TW); Chun-Chih Lin, Taipei (TW); Ren-Kun Liang, Sanchong (TW)

(73) Assignee: Forward Electronics Co., Ltd. (TW)

( * ) Notice: Subject to any disclaimer, the term of this patent is extended or adjusted under 35 U.S.C. 154(b) by 369 days.

(21) Appl. No.: 12/662,546

(22) Filed: Apr. 22, 2010

(65) Prior Publication Data

US 2011/0151107 A1   Jun. 23, 2011

(30) Foreign Application Priority Data

Dec. 22, 2009   (TW) ................................ 98144207 A

(51) Int. Cl.
 *C23C 14/54* (2006.01)
(52) U.S. Cl. ............................................. 427/9; 427/10
(58) Field of Classification Search .................. 427/8, 9, 427/10
 See application file for complete search history.

(56) References Cited

U.S. PATENT DOCUMENTS

| | | | | |
|---|---|---|---|---|
| 6,215,943 | B1 * | 4/2001 | Crotts et al. ................... | 385/137 |
| 7,247,345 | B2 * | 7/2007 | Takahashi et al. ............. | 427/162 |
| 2003/0090676 | A1 * | 5/2003 | Goebel et al. .................. | 356/504 |
| 2003/0169060 | A1 * | 9/2003 | Shinada et al. ................. | 324/751 |
| 2007/0037462 | A1 * | 2/2007 | Allen et al. ........................ | 442/5 |
| 2007/0100580 | A1 * | 5/2007 | Marcus et al. ................. | 702/170 |
| 2007/0139654 | A1 * | 6/2007 | Matsumoto et al. .......... | 356/445 |
| 2008/0139037 | A1 * | 6/2008 | Jee ................................. | 439/378 |
| 2008/0198383 | A1 * | 8/2008 | Weibel ........................... | 356/445 |
| 2009/0116020 | A1 * | 5/2009 | Wu et al. ....................... | 356/445 |

FOREIGN PATENT DOCUMENTS

| | | |
|---|---|---|
| CN | 1877298 A | 12/2006 |
| TW | 1272383 A | 2/2007 |

OTHER PUBLICATIONS

Homola, Jiri, et al., "Surface plasmon resonance sensors: review". Sensors and Actuators B 54 (1999) 3-15.*
Ekgasit, Sanong, et al., "Influence of the Metal Film Thickness on the Sensitivity of Surface Plasmon Resonance Biosensors". Applied Spectroscopy, vol. 59, No. 5, 2005, pp. 661-667.*
Akimoto, Takuo, et al., "Refractive-index and thickness sensitivity in surface plasmon resonance spectroscopy". Applied Optics, vol. 38, No. 19, Jul. 1, 1999, pp. 4058-4064.*
Patskovsky, Sergiy, et al., "Properties and sensing characteristics of surface-plasmon resonance in infrared light". J. Opt. Soc. Am. A, vol. 20, No. 8, Aug. 2003.*

* cited by examiner

*Primary Examiner* — Bret Chen
(74) *Attorney, Agent, or Firm* — Bacon & Thomas, PLLC

(57) ABSTRACT

A method for real-timely monitoring thickness change of a coating film is disclosed. In the method, a coating module having a chamber and a film thickness-monitoring module containing an SPR optical fiber sensor, a light source, a light-receiving detector, and optical fibers are first provided. The optical fibers are used to connect the SPR optical fiber sensor with the light source and the light-receiving detector. The SPR optical fiber sensor has a sensing area and is arranged in the chamber. The light source provides the SPR optical fiber sensor with light. Then, a substrate is put into the chamber. While coating process is performed on the substrate, a film is also formed on the sensing area of the SPR optical fiber sensor. The light-receiving detector receives signals output from the sensing area of the SPR optical fiber sensor and then outputs signals of light-intensity change.

9 Claims, 7 Drawing Sheets

METHOD FOR REAL-TIME MONITORING THICKNESS CHANCE OF COATING FILM

BACKGROUND OF THE INVENTION

1. Field of the Invention

The present invention relates to a coating apparatus and a method for real-timely monitoring thickness change of a coating film and, more particularly, to a coating apparatus and a method for real-timely monitoring thickness change of an organic coating film.

2. Description of Related Art

As the semiconductor technology and the industry of liquid crystal display devices develop upward, a coating process has been widely used in the domestic and foreign industries. Currently, the domestic and foreign industries are using post-production examination of a coating film. In other words, the measurement for the thickness of the coating film can only be performed after the coating process has finished and the coated sample is taken out. The quality of the resultant coating film can be recognized only after the abovementioned measurement, but not in the real-time course of the coating process. Of course, this leads to an undesirable scrapping of products when there has been a flaw in the manufacturing process. Therefore, post-production examination is not helpful to the yield of the coating process.

Previously, contact-type examination was reported. However, this type of examination still belongs to post-production examination and the coating film may be easily damaged during such. Besides, inspection using an optical system was reported. Nevertheless, such inspection is limited to a material of a substrate coated in the coating process and also can not achieve the real-time examination. Furthermore, an optical monitor system was reported, but such monitor system is limited in the precision of optical component arrangement and in the volume of the system. Thus, it is not convenient for the application of this system. In addition to the abovementioned, a piezoelectric detection technology of quartz crystal microbalance (QCM) was reported. Although this technology seems to realize the real-time monitoring, the detection system and components cannot be used in a vacuum chamber, and thus real-time monitoring for a coating film still cannot be accomplished in a mass production at present.

The aforesaid technologies mostly are applied in thickness detection of an inorganic coating film. Nonetheless, referring to thickness detection of an organic coating film, there is no useful technology presently. If the detection reaches to nano-scale detection of a film thickness, the detection system is expensive.

In view of the mentioned above, if a technology to detect nano-scale thickness of a coating film and the technology can achieve real-time monitoring, loss reduction of failed processes, deposition monitoring of an organic film, simple operation, and low costs, it will be beneficial for the development of semiconductor-related technologies.

SUMMARY OF THE INVENTION

The object of the present invention is to provide a method for real-timely monitoring thickness change of a film. The utilization of an optical fiber sensor which has small volume, is not influenced by an electromagnetic wave, and can be arranged in a vacuum chamber, is to realize the real-time monitoring, loss reduction of failed processes, and deposition monitoring of an organic film.

Another object of the present invention is to provide a coating apparatus for real-time monitoring. The coating apparatus combines a general coating module with an optical fiber sensor, and accomplishes high-sensitivity detection, loss reduction of failed processes, and being suitable for thickness detection of a nano-scale, organic, and inorganic film.

To achieve the objects, a method for real-timely monitoring thickness change of a film is provided in an aspect of the present invention. The method includes providing a coating module having a chamber, and a thickness-monitoring module containing a surface plasmon resonance (SPR) optical fiber sensor, a light source, a light-receiving detector, and a plurality of optical fibers, wherein the optical fibers connect the SPR optical fiber sensor with the light source and the light-receiving detector; the SPR optical fiber sensor has a sensing area and is arranged in the chamber; and the light source provides the sensing area of the SPR optical fiber sensor with light; putting a substrate into the chamber of the coating module; performing a coating process on the substrate while a film is formed on the sensing area of the SPR optical fiber sensor; and utilizing the light-receiving detector to receive signals output from the sensing area of the SPR optical fiber sensor and then to output signals of light-intensity change.

The aforesaid method of the present invention further includes providing a micro-processing unit, wherein the micro-processing unit has a thickness conversion database, receives the signals of the light-intensity change output from the light-receiving detector, converts the signals of the light-intensity change into thickness of the film according to the thickness conversion database, and outputs the dimension regarding the thickness of the film.

In another aspect of the present invention, a coating apparatus for real-time monitoring is provided. The coating apparatus includes a coating module having a chamber, and a thickness-monitoring module containing a surface plasmon resonance (SPR) optical fiber sensor, a light source, a light-receiving detector, and a plurality of optical fibers, wherein the optical fibers connect the SPR optical fiber sensor with the light source and the light-receiving detector; the SPR optical fiber sensor has a sensing area and is arranged in the chamber; the light source provides the sensing area of the SPR optical fiber sensor with light; and the light-receiving detector receives signals output from the sensing area of the SPR optical fiber sensor and then outputs signals of light-intensity change.

In the coating apparatus of the present invention, the thickness-monitoring module further contains a micro-processing unit, wherein the micro-processing unit has a thickness conversion database, receives the signals of the light-intensity change output from the light-receiving detector, converts the signals of the light-intensity change into thickness of the film according to the thickness conversion database, and outputs the dimension regarding the thickness of the film.

Preferably, while a coating process is being performed on a substrate, a film is also formed on the sensing area of the SPR optical fiber sensor.

In the method and the coating apparatus of the present invention, any kind of light source can be used as the light source of the present invention, for example, a halogen light source, a laser diode, and a light emitting diode (LED). Accordingly, the light source can output single-wavelength light or multi-wavelength light. If the light source provides single-wavelength light, an optical power meter can be used as the light-receiving detector to detect light intensity. Hence, in the course of the coating process, the thickness change of the coating film can be determined by the light-power change output and shown by the optical power meter. Alternatively, if the light source provides multi-wavelength light, a spectrometer can be used as the light-receiving detector to detect light intensity. Hence, in the course of the coating process, the thickness change of the coating film can be determined by the spectrogram change (i.e. dip-shift) output and shown by the spectrometer.

In the abovementioned method and coating apparatus of the present invention, the usable SPR optical fiber sensor can comprise a core layer, a coating layer enclosing the core layer, a fillister exposing the core layer, and a pre-coated layer locating on the core layer exposed by the fillister. The fillister serves as the sensing area, and can be formed by any method, preferably by side-polishing or etching. The relative positions of the SPR optical fiber sensor and the substrate in the chamber of the coating module, are not specifically limited, and can be determined according to different situations. For example, the SPR optical fiber sensor can be arranged outside the substrate, near a side of the substrate, in the center of the substrate, in an invalid zone of the substrate (such as a zone for cutting) and so forth.

Furthermore, the optical fibers utilized in the present invention can be for example, single-mode or multi-mode optical fibers. If optical fiber connectors are required to connect the fibers with the SPR optical fiber sensor, the light source, and the light-receiving detector, the coating apparatus and the method of the present invention can further comprise the optical fiber connectors. The utilizable optical fiber connectors of the present invention can be FC, ST or LC connectors for example.

Accordingly, due to the properties of the optical fibers such as small volume and not being influenced by electromagnetic waves, the present invention arranges the SPR optical fiber sensor in the vacuum chamber of the coating apparatus to connect to an outside detection system. As an organic or inorganic material is deposited on the sensor, the signal of the SPR changes. Such change of the SPR signal is monitored by the outside detection system, and thus the thickness of the coating layer can be real-timely analyzed and demonstrated. Hence, unlike a conventional technique such as QCM piezoelectric detection which cannot measure organic or nano-scale coating film and thus a sampling inspection needs to be performed after a batch of manufacturing, the present invention can be applied in thickness detection of inorganic and organic coating films and achieves the purpose of real-time monitoring to reduce the loss of the failed processes and to increase the yield.

Other objects, advantages, and novel features of the invention will become more apparent from the following detailed description when taken in conjunction with the accompanying drawings.

DETAILED DESCRIPTION OF THE PREFERRED EMBODIMENT

Figure 1A:
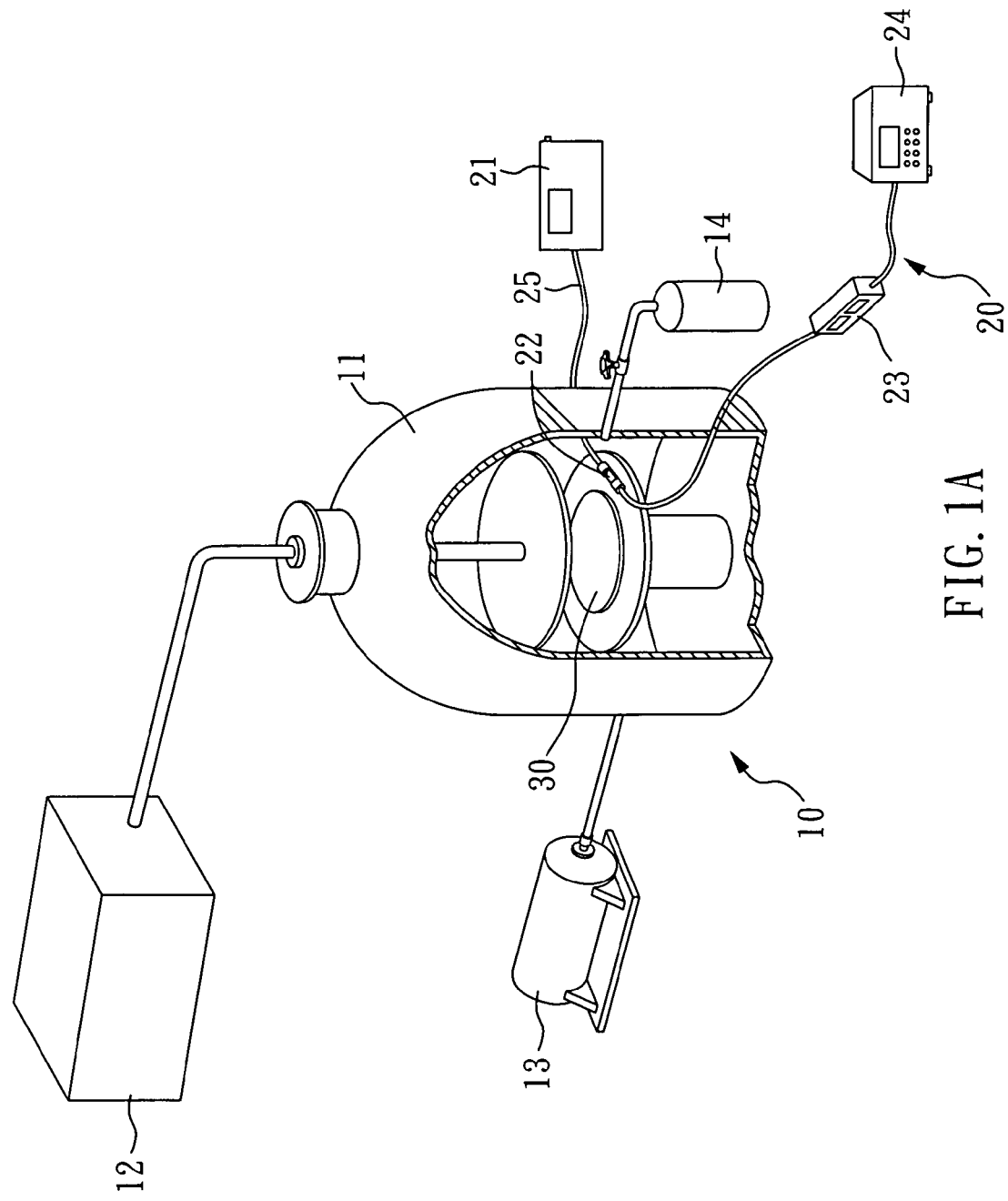
FIG. 1A shows a perspective view of the coating apparatus for real-timely monitoring thickness changes in the example of the present invention.

Because of the specific embodiments illustrating the practice of the present invention, one skilled in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

The drawings of the embodiments in the present invention are all simplified charts or views, and only reveal elements relative to the present invention. The elements revealed in the drawings are not necessarily aspects of the practice, and quantity and shape thereof are optionally designed. Further, the design aspect of the elements can be more complex.

Example

FIG. 1A shows a perspective view of the coating apparatus for real-timely monitoring thickness changes in the example of the present invention. As shown in FIG. 1A, the coating apparatus of the present invention for real-timely monitoring includes a coating module 10 and a thickness-monitoring module 20.

The coating module 10 includes a chamber 11, a radio frequency (RF) plasma generator 12, a vacuum pump 13, and a coating-material supply 14. The RF plasma generator 12, the vacuum pump 13, and the coating-material supply 14 are connected to the chamber 11. The vacuum pump 13 serves to remove the air in the chamber 11. The coating-material supply 14 is used to provide a material of coating films, for example, isopropanol. Under the operation of the RF plasma generator 12, a coating process is performed on a surface of a substrate 30.

Besides, the thickness-monitoring module 20 contains a light source 21, an SPR optical fiber sensor 22, a light-receiving detector 23, a micro-processing unit 24, and a plurality of optical fibers 25. The optical fibers 25 connect the SPR optical fiber sensor 22 with the light source 21 and the light-receiving detector 23. The SPR optical fiber sensor 22 has a sensing area SA and is arranged in the chamber 11 of the coating module 10. The light source 21 provides the sensing area SA of the SPR optical fiber sensor 22 with light. The light-receiving detector 23 receives signals output from the sensing area SA of the SPR optical fiber sensor 22 and then outputs signals of light-intensity change. In the present example, the SPR optical fiber sensor 22 is arranged by the side of the substrate 30, but is not limited thereto.

The micro-processing unit 24 electrically connects the light-receiving detector 23 and thus can receive the signals of the light-intensity change output from the light-receiving detector 23. In addition, the micro-processing unit 24 has a thickness conversion database. Therefore, the micro-processing unit 24 can convert the signals of the light-intensity change into thickness of the film formed on the sensing area SA of the SPR optical fiber sensor 22 according to the thickness conversion database, and outputs the dimension regarding the thickness of the film.

Figure 1B:
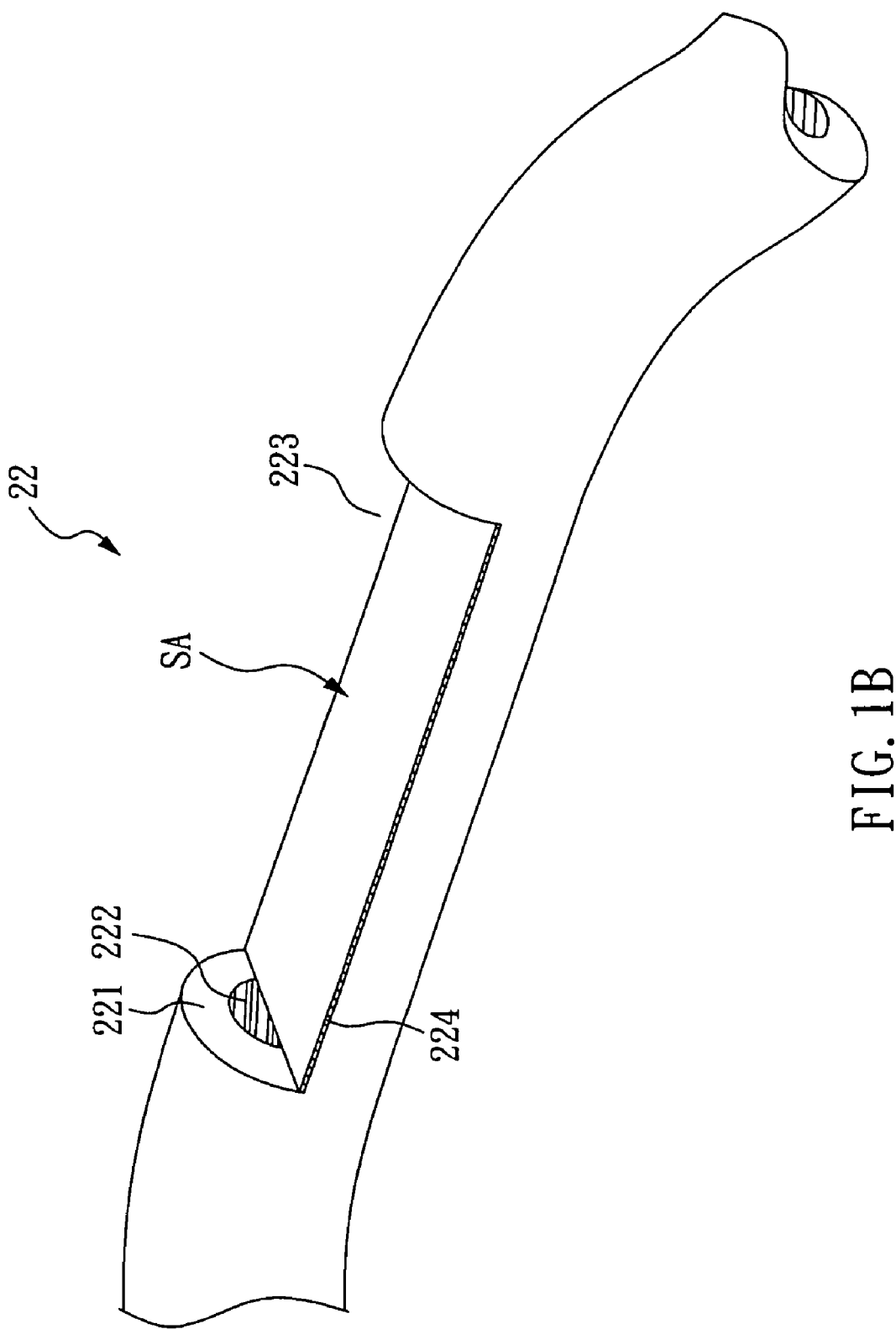
FIG. 1B shows an enlarged view of one aspect of the SPR optical fiber sensor in the example of the present invention.

FIG. 1B shows an enlarged view of one aspect of the SPR optical fiber sensor 22. As shown in FIG. 1B, the SPR optical fiber sensor 22 includes a core layer 222, a coating layer 221 enclosing the core layer 222, a fillister 223 exposing the core layer 222, and a gold layer 224 locating on the core layer 222 exposed by the fillister 223. The fillister 223 can be formed by side-polishing or etching. The gold layer 224 can be deposited on the core layer 222 in the fillister 223 by DC sputtering, RF sputtering, or any other method. The gold layer 224 is not limited in specific thickness, and can be in a range from 30 nm to 50 nm. The gold layer 224 can be selectively arranged, i.e. the SPR optical fiber sensor 22 can has no gold layer. However, the deposition of the gold layer 224 can enhance the SPR effect. In the abovementioned SPR optical fiber sensor 22, the location of the fillister 223 and the gold layer 224 is used as the sensing area SA.

Figure 1C:
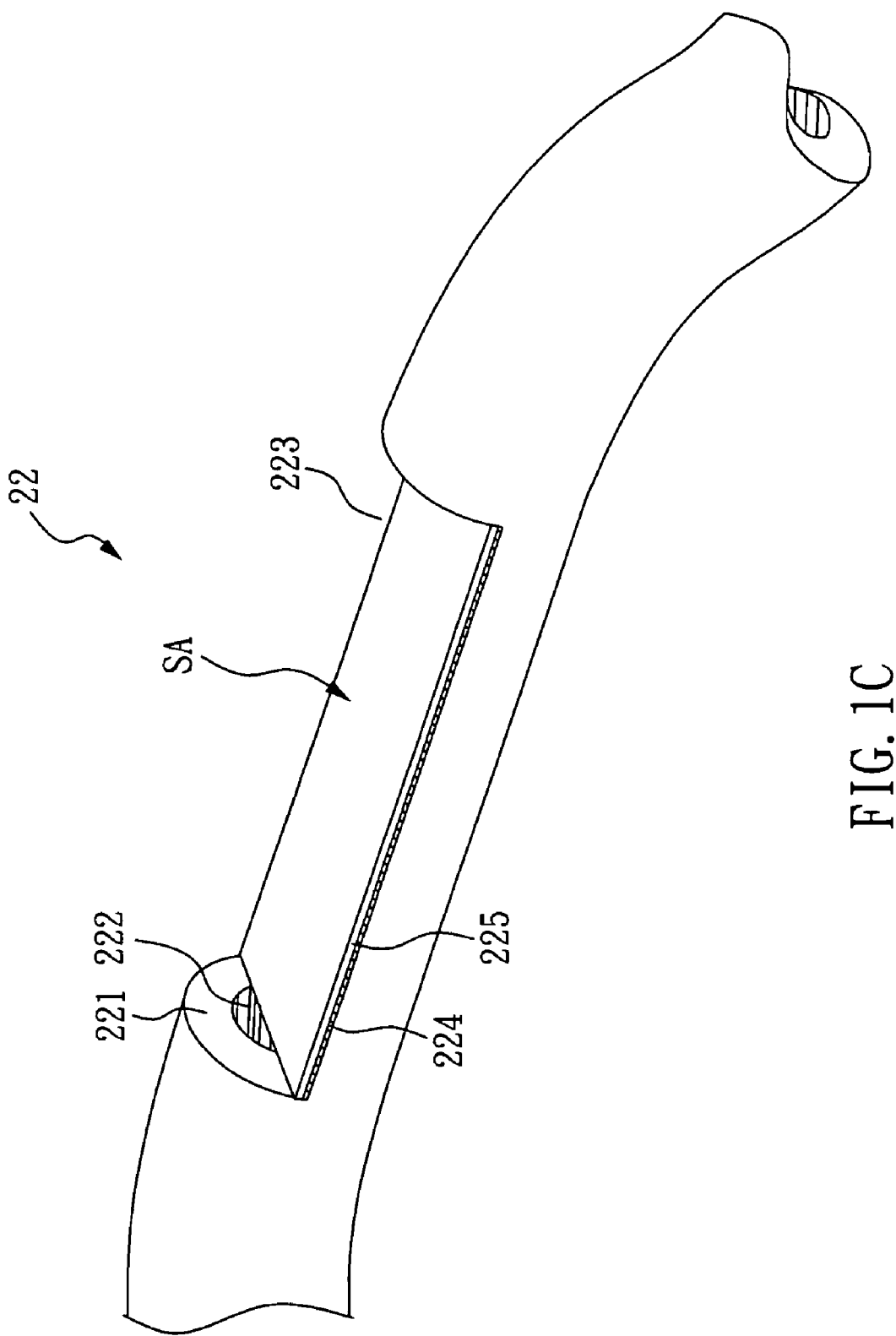
FIG. 1C shows an enlarged view of another aspect of the SPR optical fiber sensor in the example of the present invention.

FIG. 1C shows an enlarged view of another aspect of the SPR optical fiber sensor 22. As shown in FIG. 1C, the SPR optical fiber sensor 22 includes a core layer 222, a coating layer 221 enclosing the core layer 222, a fillister 223 exposing the core layer 222, a gold layer 224 locating on the core layer 222 exposed by the fillister 223, and a pre-coated layer 225 locating on the gold layer 224. The formation of the fillister 223 and the gold layer 224 can be the same as the abovementioned. The pre-coated layer 225 is formed of the material of the coating film in predetermined thickness, and thus is advantageous for the SPR optical fiber sensor 22 to detect the thickness of the coating film.

Test Example 1

Real-time monitoring of the thickness change of an organic coating film is described below.

First, a coating apparatus is provided. The coating apparatus includes a coating module 10 and a thickness-monitoring module 20. The coating module 10 has a chamber 11. The thickness-monitoring module 20 contains a light source 21, an SPR optical fiber sensor 22, a light-receiving detector 23, a micro-processing unit 24, and a plurality of optical fibers 25. The SPR optical fiber sensor 22 is arranged in the chamber 11 of the coating module 10. The optical fibers 25 serve to connect the SPR optical fiber sensor 22 with the light source 21 and the light-receiving detector 23. The light source 21 provides the SPR optical fiber sensor 22 with light via the optical fibers 25. The residual structure of the coating apparatus can accord with that of the abovementioned example.

After a substrate 30 is put into the chamber 11 of the coating module 10, the operation of the coating apparatus starts. The steps of the operation contains conventional coating steps such as turning on the RF plasma generator 12, the vacuum pump 13, the coating material supply 14, the light source 21, the light-receiving detector 23, the micro-processing unit 24 and so on. In the present Test Example, the coating-material supply 14 is filled with isopropanol.

Subsequently, a coating process is performed on a surface of the substrate 30 to form an organic film (COOH⁻) while the organic film is also formed on the sensing area SA of the SPR optical fiber sensor 22. In the course of the coating process, the light-receiving detector 23 can real-timely receive the signals output from the sensing area SA of the SPR optical fiber sensor 22 and then output the light-intensity change. In the present Test Example, the light source 21 is a multi-wavelength halogen light source, and the light-receiving detector 23 is a spectrometer. Therefore, spectrograms are output during the coating process. Additionally, in order to recognize the relation between the test results from the SPR optical fiber sensor and the actual thickness of the coating film after deposition, an α-step profiler is used to measure the actual thickness of the organic film.

Figure 2A:
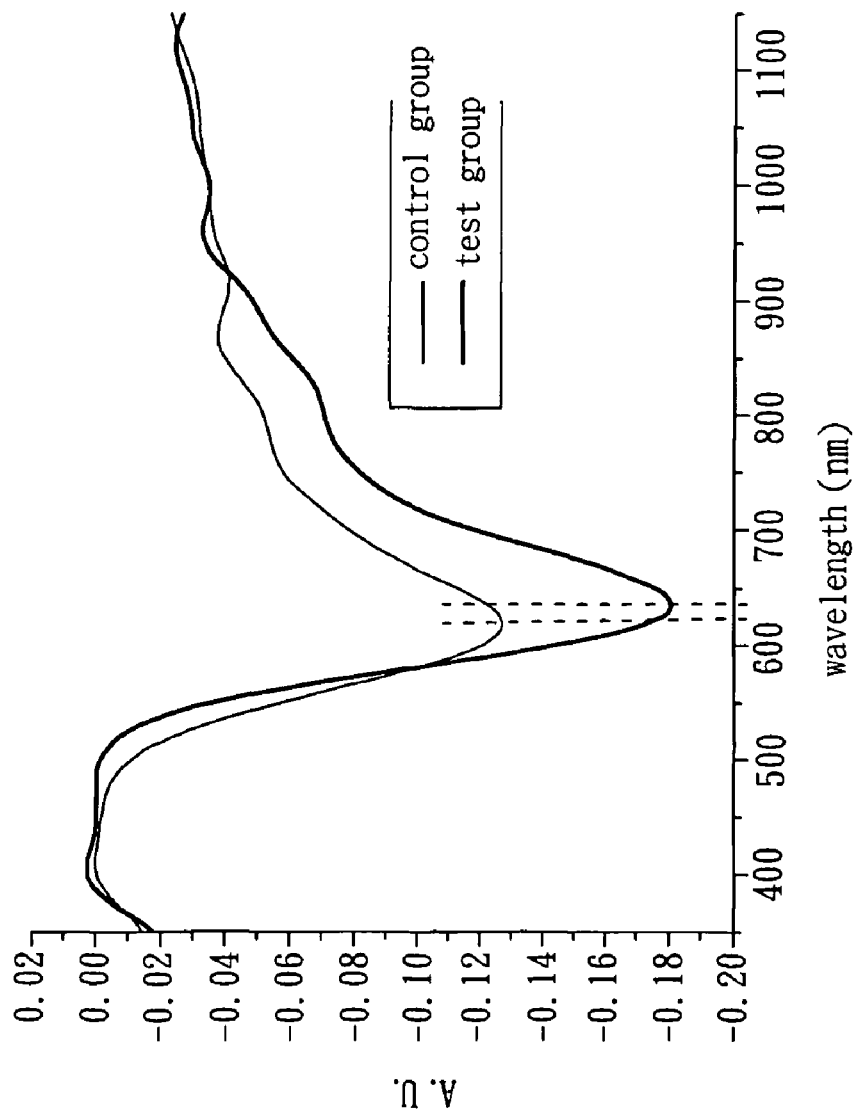
FIG. 2A shows comparative spectrograms with or without organic-film deposition in Test Example 1 of the present invention.

FIG. 2A shows comparative spectrograms of with or without organic-film deposition. The test group is the spectrogram of the isopropanol organic film obtained by plasma deposition for 5 minutes. The result shows that the deposition of the organic film truly causes the dip shift of the SPR wavelength on the sensing area SA of the SPR optical fiber sensor 22.

Figure 2B:
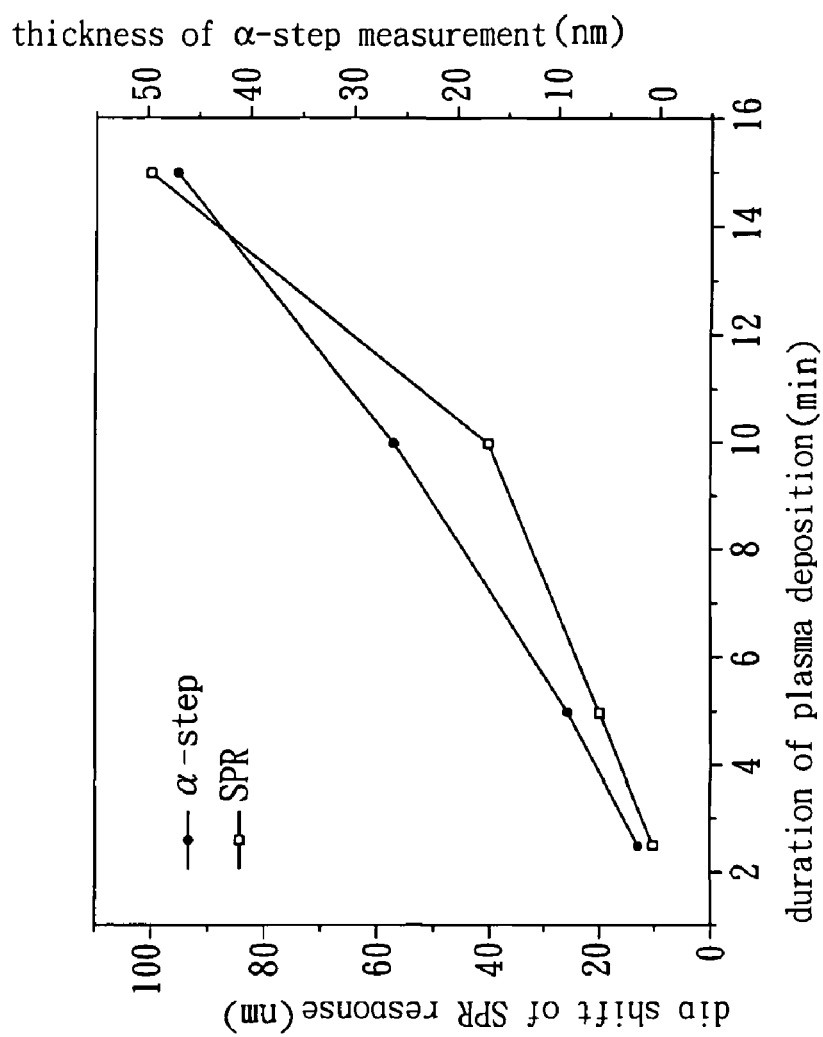
FIG. 2B shows the relation between the dip shift and the α-step result of the different deposition time in Test Example 1 of the present invention.

FIG. 2B shows the relation between the dip shift and the α-step result of the different deposition time. The result shows the organic film with nano-scale thickness and a corresponding dip shift of the SPR wavelength. Even though the thickness of the organic film is nano-scale, the corresponding dip shift of the SPR wavelength is still demonstrated in the spectrogram. Therefore, the SPR optical fiber sensor has nano-scale detection ability in regard to the thickness of the coating film.

Test Example 2

In the present test example, real-time monitoring of the thickness change of an inorganic coating film is performed in a similar manner of Test Example 1 except the differences described below. Since the process is to deposit the inorganic coating film on the surface of the substrate 30, an inorganic material such as $TiO_2$ is used. In addition, the process needs to be adjusted according to conventional techniques and performed in an atmosphere of inert gas such as argon. Furthermore, the gold layer 244 is deposited on the sensing area SA of the SPR optical fiber sensor 22 used in the present test example.

Figures 3A, 3B:
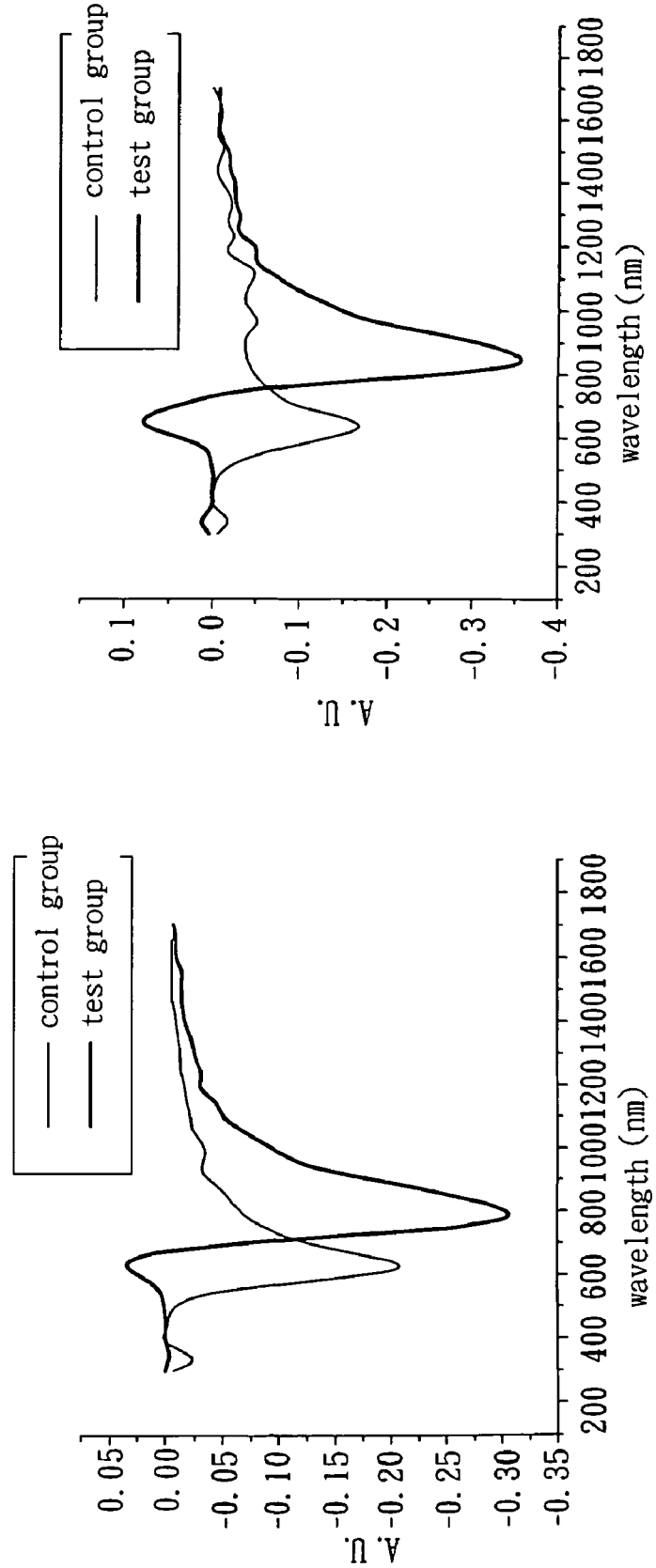
FIG. 3A shows comparative spectrograms with or without $TiO_2$ inorganic film (20 nm) deposition in Test Example 2 of the present invention.
FIG. 3B shows comparative spectrograms with or without $TiO_2$ inorganic film (30 nm) deposition in Test Example 2 of the present invention.

FIGS. 3A and 3B show spectrograms with or without the deposition of $TiO_2$ inorganic film. In the figures, the control groups are the spectrograms without inorganic film deposition. In FIG. 3A, the test group is the spectrogram of 20 nm $TiO_2$ inorganic film. In FIG. 3B, the test group is the spectrogram of 30 nm $TiO_2$ inorganic film. The results show that the deposition of the $TiO_2$ inorganic film truly makes the dip shift of the SPR wavelength on the sensing area SA of the SPR optical fiber sensor 22. As the thickness of the $TiO_2$ inorganic film increases, the dip shift of the SPR wavelength also increases.

Test Example 3

Figure 4:
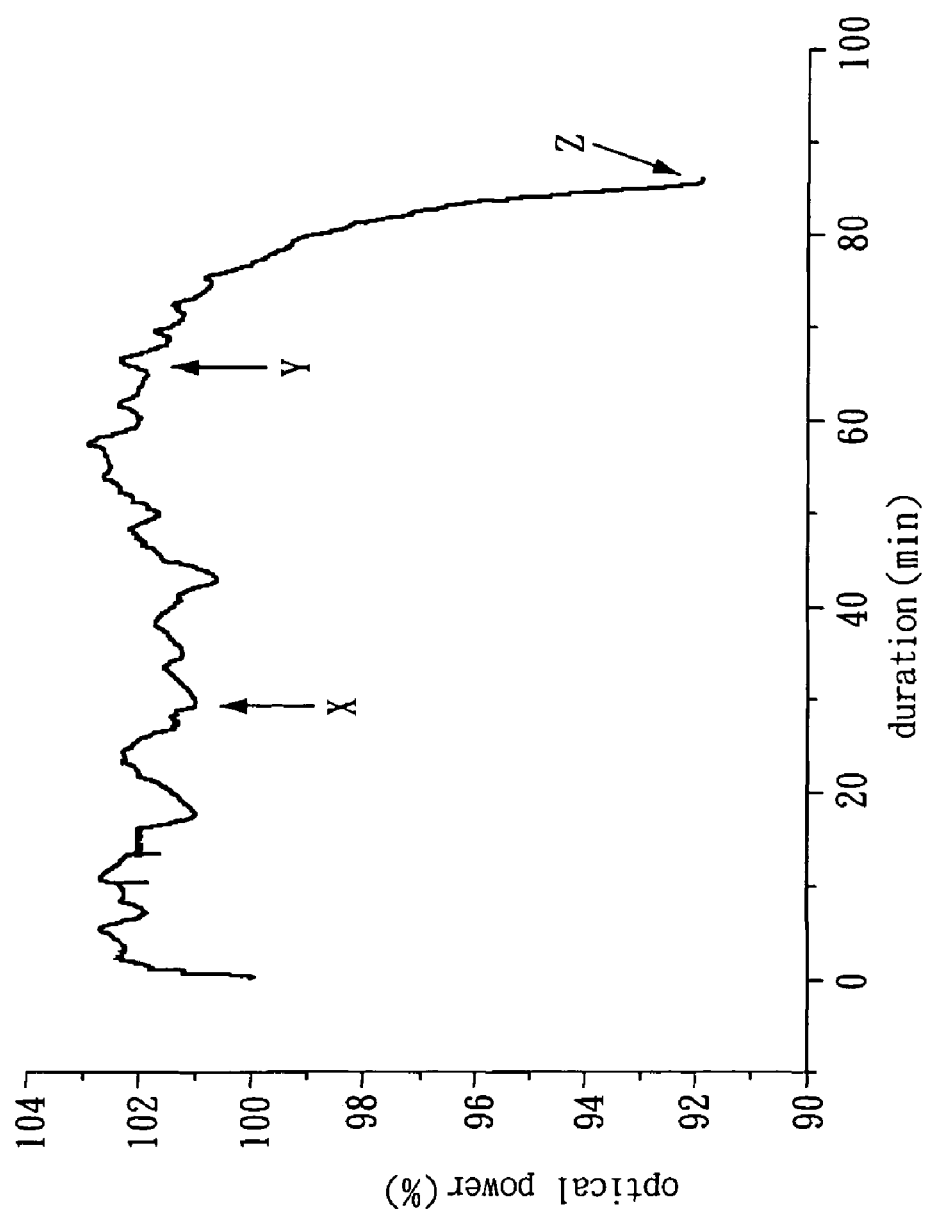
FIG. 4 shows optical powder change for real-timely monitoring $TiO_2$ inorganic film deposition in Test Example 3 of the present invention.

In the present test example, real-time monitoring of the thickness change of an inorganic coating film is performed in a similar manner of Test Example 2 except the differences described below. The present test example uses a laser light source as the light source 21 and an optical power meter as the light-receiving detector 23 for real-time monitoring. The result is shown in FIG. 4 where y-axis represents the intensity of the optical power and x-axis represents the duration of the coating process. In addition, X, Y, and Z respectively stand for the time points of removing air until vacuum, $TiO_2$ deposition, and sputtering cessation. The result demonstrates some undulation due to poor junction at the time point X. However, when $TiO_2$ deposition begins at the time point Y, optical power gradually decreases as duration of deposition increases until the deposition stops. Accordingly, the present invention can realize real-time monitoring in the course of the coating process.

Consequently, the present invention can detect optical changes to achieve the purpose of real-time monitoring whether organic or inorganic film deposition is performed.

Although the present invention has been explained in relation to its preferred embodiment, it is to be understood that many other possible modifications and variations can be made without departing from the scope of the invention as hereinafter claimed.

What is claimed is:

1. A method for real-timely monitoring thickness change of a film, comprising:

providing a coating module having a chamber, and a thickness-monitoring module comprising a surface plasmon resonance (SPR) optical fiber sensor, a light source, a light-receiving detector, and a plurality of optical fibers, wherein the optical fibers connect the SPR optical fiber sensor with the light source and the light-receiving detector; the SPR optical fiber sensor has a sensing area and is arranged in the chamber; and the light source provides the sensing area of the SPR optical fiber sensor with light;

putting a substrate into the chamber of the coating module;

performing a coating process on the substrate while a film is formed on the sensing area of the SPR optical fiber sensor; and utilizing the light-receiving detector to receive signals output from the sensing area of the SPR optical fiber sensor and then to output a signal of a light-intensity change.

2. The method as claimed in claim 1, further comprising: providing a micro-processing unit, wherein the micro-processing unit has a thickness conversion database, receives the signals of the light-intensity change output from the light-receiving detector, converts the signals of the light-intensity change into thickness of the film according to the thickness conversion database, and outputs a dimension regarding the thickness of the film.

3. The method as claimed in claim 1, wherein the light source outputs single-wavelength light.

4. The method as claimed in claim 3, wherein the signal of light-intensity change output from the light-receiving detector is light-power change.

5. The method as claimed in claim 4, wherein the light-receiving detector is an optical power meter.

6. The method as claimed in claim 1, wherein the light source outputs multi-wavelength light.

7. The method as claimed in claim 6, wherein the signal of light-intensity change output from the light-receiving detector is a spectrogram.

8. The method as claimed in claim 7, wherein the light-receiving detector is a spectrometer.

9. The method as claimed in claim 1, wherein the SPR optical fiber sensor comprises a core layer, a coating layer enclosing the core layer, a fillister exposing the core layer, and a pre-coated layer locating on the core layer exposed by the fillister, and the fillister is the sensing area.

* * * * *

UNITED STATES PATENT AND TRADEMARK OFFICE
CERTIFICATE OF CORRECTION

PATENT NO. : 8,377,503 B2  Page 1 of 1
APPLICATION NO. : 12/662546
DATED : February 19, 2013
INVENTOR(S) : Yu-Chia Tsao et al.

It is certified that error appears in the above-identified patent and that said Letters Patent is hereby corrected as shown below:

On the Title Page, Item (54) and in the Specification, Column 1, Lines 1-2, Title should read "Method for Real-Time Monitoring Thickness ~~Chance~~ Change of Coating Film"

Signed and Sealed this
Eighteenth Day of June, 2013

Teresa Stanek Rea
*Acting Director of the United States Patent and Trademark Office*